(12) United States Patent
Subkowski et al.

(10) Patent No.: US 6,365,155 B1
(45) Date of Patent: Apr. 2, 2002

(54) ANCROD-SPECIFIC MONOCLONAL ANTIBODIES, ANTIBODY FRAGMENTS, MIXTURES OR DERIVATIVES THEREOF AND USE OF THE SAME

(75) Inventors: Thomas Subkowski, Mutterstadt; Wilfried Hornberger, Neustadt, both of (DE)

(73) Assignee: Abbott Laboratories, Abott Park, IL (US)

( * ) Notice: Subject to any disclaimer, the term of this patent is extended or adjusted under 35 U.S.C. 154(b) by 0 days.

(21) Appl. No.: 09/446,983

(22) PCT Filed: Jun. 23, 1998

(86) PCT No.: PCT/EP98/03834

§ 371 Date: Dec. 30, 1999

§ 102(e) Date: Dec. 30, 1999

(87) PCT Pub. No.: WO99/02564

PCT Pub. Date: Jan. 21, 1999

(30) Foreign Application Priority Data

Jul. 10, 1997 (DE) .......................... 197 29 544

(51) Int. Cl.[7] ...................... A61K 39/395; C07K 16/36; G01N 33/573; G01N 33/53; C12N 5/06

(52) U.S. Cl. ................ 424/146.1; 424/145.1; 435/7.4; 435/7.8; 435/337; 435/338; 530/388.25; 530/388.26

(58) Field of Search ............... 530/388.25, 388.26; 424/146.1, 145.1; 435/337, 7.8, 7.4, 338

(56) References Cited

FOREIGN PATENT DOCUMENTS

| | | |
|---|---|---|
| CA | 2004764 | 6/1990 |
| EP | 395 375 | 10/1990 |
| EP | 556 906 | 8/1993 |
| EP | 592 903 | 4/1994 |
| WO | 90/06362 | 6/1990 |

OTHER PUBLICATIONS

Critical Reviews in Oncology/Hematology 15 (1993) 23–33.
Thrombosis Res. vol. 6, 189–194, 1975.
FEBS vol. 297, No. 3, 297–301; Burkhart et al.
Jr. Vascular Surgery, vol. 17, No. 2, Colet et al.288–292.
Nat. vol. 256, Aug. 7, 1997, 495–497.
Thromb Haemostas (Stuttgart)50(2) 604–609(1983) Latallo.
Abaza et al. J. of Protein Cemistry 11(5):433–444, 1997.*
Campbel Monoclonal Technology, Chapter 1, Elsevier Science Publishers, Netherlands, pp. 1–32, 1985.*
Edwards P. A. W. Biochem. J. 200:1–10, 1981.*

* cited by examiner

Primary Examiner—David Saunders
Assistant Examiner—Amy DeCloux
(74) Attorney, Agent, or Firm—Keil & Weinkauf

(57) ABSTRACT

Ancrod-specific monoclonal antibodies, antibody fragments, mixtures or derivatives thereof are used in pharmaceutical preparations and in diagnosis. Cells which express these antibodies, antibody fragments, mixtures or derivatives thereof are also disclosed.

10 Claims, 1 Drawing Sheet

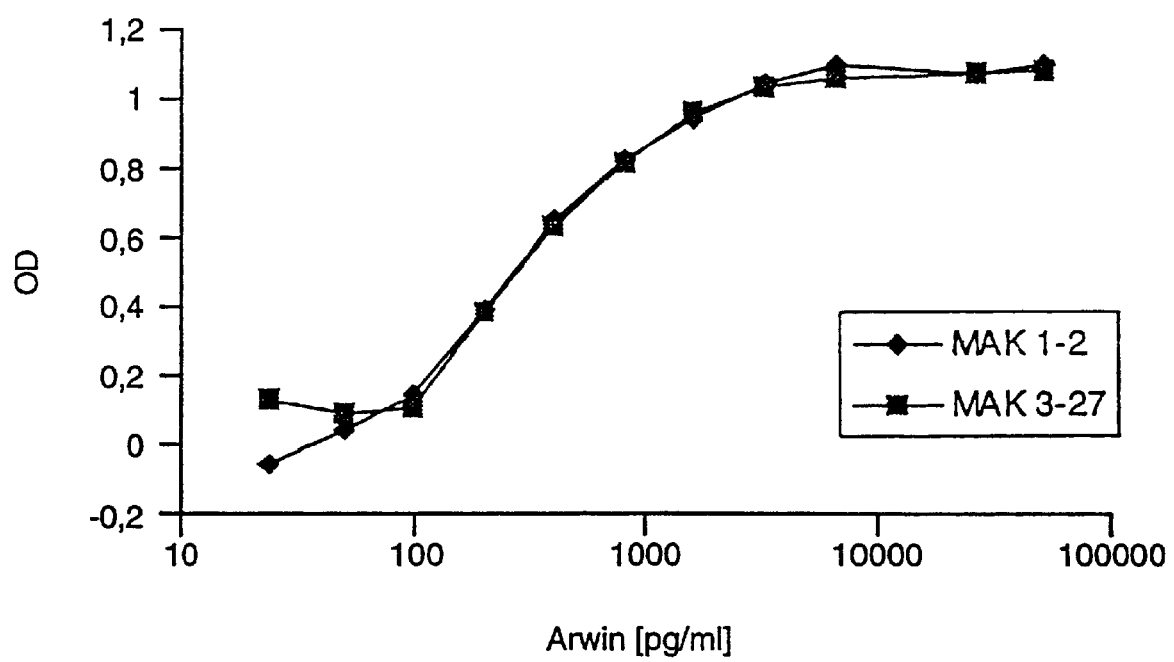

ANCROD-SPECIFIC MONOCLONAL ANTIBODIES, ANTIBODY FRAGMENTS, MIXTURES OR DERIVATIVES THEREOF AND USE OF THE SAME

FIELD OF THE INVENTION

The invention relates to ancrod-specific monoclonal antibodies, antibody fragments, mixtures or derivatives thereof and their use in pharmaceutical preparations or in diagnosis, and to pharmaceutical preparations which comprise these antibodies, antibody fragments, mixtures or derivatives thereof.

The invention furthermore relates to cells which express these antibodies, antibody fragments, mixtures or derivatives thereof.

BACKGROUND OF THE INVENTION

Ancrod (proprietary name: Arwin®, Arvin®) is an enzyme from the venom of the Malayan pit viper (Agkistrodon rhodostoma). It is a highly glycosylated serine protease which has an average MW of about 38000 and which has anticoagulant properties and the ability to dissolve blood clots.

Normal coagulation of blood is effected by thrombin which eliminates fibrinopeptides A and B from the fibrinogen molecule and thus leads to the formation of fibrin (EP-B-0 556 906), the main constituent of thrombi in addition to, for example, red blood corpuscles or platelets. In contrast to thrombin, acrod cleaves only the arginine-glycine linkage in the a("A") chain of the fibrinogen molecule, which liberates fibrinopeptides A, AP and AY (Cole et al., J. Vascular. Surgery, Vol 17, 1993: 288–292). The β(B) chain of the fibrinogen molecule is not attacked by ancrod and is thus not liberated. The fragments (de-"A"-fibrin monomers) produced after the elimination of the fibrinopeptides caused by ancrod are eventually able to polymerize to thin filaments. The resulting atypical, soluble fibrin is lyzed by endogenous plasmin and/or removed by the reticuloendothelial system (=RES, monocyte/macrophage system). Further cleavage of the de-"A"-fibrinogen molecule by thrombin to give natural fibrin no longer takes place because the resulting molecule is not a thrombin substrate.

Ancrod causes a dose-dependent decrease in the blood fibrinogen concentration. Therapeutically induced and controlled hypofibrinogenemia diminishes the plasma viscosity and tendency of erythrocytes to aggregate so far that the flow properties of the blood are crucially improved. This provides the condition for greater flow of blood through stenosed vessels. Ancrod is currently used to treat, for example, chronic disturbances of peripheral arterial blood flow, and is undergoing clinical phase III studies on stroke.

Ancrod is advantageously injected subcutaneously. Treatment can take place in hospital or, if the regular checks of the fibrinogen concentration necessary to monitor the therapy are ensured, also on an outpatient basis. Intravenous administration of ancrod is possible but should take place only in exceptional cases and under hospital observation.

The dosage of ancrod must also be individualized. The behavior of the fibrinogen concentration as a function of the ancrod dose is crucial. It must be slowly reduced to 70–100 mg/100 ml of plasma (=therapeutic range). The fibrinogen concentration must be adjusted to be within this range throughout the treatment period. The flow properties of the blood are satisfactory under these conditions. The therapy normally lasts 3–4 weeks but can, if necessary, be extended beyond this period.

On subcutaneous administration, 70 I.U. (=international units, 1 ml) are given each day in the first 4 days, and 70–140 I.U. are given, depending on the behavior of the fibrinogen concentration, from day 5 onwards. If the fibrinogen concentration is in the therapeutic range, single injections of 210–280 I.U. are given 2–3 times a week.

On intravenous infusion, initially 2–3 I.U./kg of body weight are given over the course of eight hours. The subsequent dosage of ancrod depends on the fibrinogen concentration attained. It is generally sufficient to inject a further 1 I.U./kg of body weight slowly every 12 hours.

The initial half-life of ancrod in the circulation is about 3–5 hours, but slows down as the concentration falls so that after about 4 days, within this time in general 90% of the administered ancrod are eliminated, the half-life is extended to 9–12 days.

Although ancrod contrasts with, for example, heparin and warfarin in being associated with fewer problems of unspecific bleeding during the treatment (see Z. S. Latallo, "Retrospective Study on Complications and Adverse Effects of Treatment with Thrombin-Like Enzymes—A Multicenter Trial", Thromb. Haemostasis, 50 (1983) 604–609), specific treatment of such bleeding is necessary and desirable.

Contraindications for treatment with ancrod are, for example, hemorrhagic diathesis, danger of bleeding associated with injuries, after operations and deliveries, for ulcerative intestinal disorders, neoplasms, poorly controllable hypertension, acute cerebral infarct and active pulmonary tuberculosis, dysfunctions of the RES and disturbances of clot breakdown, eg. in states of high fever, severe liver disorders, manifest and incipient states of shock or pregnancy.

As described above, the risk of bleeding is relatively low with ancrod when the fibrinogen concentration is reduced slowly and is adjusted to 70–100 mg/100 ml during the period of therapy. Patients with a latent tendency to bleed, eg. cases of kidney stones or renal failure, should be monitored particularly carefully. Arterial punctures and intramuscular injections of other drugs should be avoided. Caution is necessary on concurrent administration of RES-blocking and ulcerogenic drugs, anticoagulants, antifibrinolytics, thrombolytics and medicines which inhibit platelet aggregation, and on intramuscular administration of ancrod. Absorption from the muscle depot generally takes place very quickly so that too many de-"A"-fibrin monomers flow away and there is a danger of thromboembolic complications.

The total incidence of bleeding in a study on 429 patients (Crit. Rev. Oncol. Hematol. 15 (1993) 23–33), who received ancrod without previous thrombolytic therapy was 9.8% (4.2% internal bleeding; 5.6% external bleeding).

Currently used to neutralize the enzymatic activity of ancrod is an antidote based on an immunoglobulin preparation from goat serum (Knoll AG publication, June 1983, entitled Arwin®). This antidote consisting of polyclonal antibodies is used in cases of severe hemorrhagic complications or increased danger of bleeding, eg. associated with accident injuries or because surgery suddenly becomes indicated. Neutralization of ancrod should be followed by administration of 4–5 g of human fibrinogen. If human fibrinogen, plasma or blood is administered without previous neutralization of ancrod by an antidote, there is a danger of acute disseminated coagulation.

Stocker et al (Thrombosis Research, Vol. 6, 1975: 189–194) investigated thrombogenesis in the presence of Arwin® alone and in the presence of the polyclonal antidote and were able to demonstrate the antidote effect.

Besides this use of polyclonal antibodies from goats, EP-B-0 395 375, EP-B-0 556 906 and Burkhardt et al (FEBS, Vol 297, No. 3, 1992: 297–301) describe monoclonal or polyclonal antibodies for detecting expression of ancrod genes, for detecting fibrinogen in blood using ancrod and ancrod antibodies or purification of ancrod using antibodies.

A disadvantage of the goat polyclonal antibodies used as ancrod antidote is that, for example, they consist of a mixture of antibodies, many of which have no ancrod-neutralizing effect. This large number of different antibodies may lead to a rapid immune response and, moreover, leads to a relatively low ancrod-neutralizing capacity. In addition, the antidote contains antibodies of varying affinity for ancrod. Polyclonal antibodies can, because they are obtained from animals, be standardized only with difficulty, which means that there are variations in the different production batches.

SUMMARY OF THE INVENTION

It is an object of the present invention to develop an antidote to ancrod which does not have the abovementioned disadvantages and is easy to produce industrially.

We have found that this object is achieved by the novel monocloncal antibodies, antibody fragments, mixtures or derivatives thereof which bind to ancrod and inhibit its activity, where the binding affinity is in a range from $1\times10^{-7}$ to $1\times10^{-12}$ M, and the neutralizing effect is improved at least 100% by comparison with goat polyclonal antibodies in vivo.

BRIEF DESCRIPTION OF DRAWINGS

FIG. 1 is a graph depicting the quantification of ancord (proprietary name Arwin) by optical density with antibodies Mab 1-2 and Mab 3-27.

DETAILED DESCRIPTION OF THE INVENTION

The novel antibodies used as ancrod antidote advantageously have a number of improved properties. For example, they form a homogeneous, well-characterized product consisting of one antibody or one antibody subclass showing no variations between different production batches. They can be produced in any desired quantity, and production thereof does not entail any risk of viral or bacterial contamination because they are not produced in animals. The novel antibodies, antibody fragments, mixtures or derivatives thereof are epitope-specific and show a high binding and neutralizing activity. They can therefore be administered in small amounts for treatment. The homogeneity of the product together with the smaller amounts used, owing to the high binding and neutralizing activity, result in a marked reduction in the risk of an immune response in the patient. Variations in the binding and neutralizing activity like those with polyclonal antibodies do not occur within the various antibodies, antibody fragments or derivatives. Mixing different monoclonal antibodies, antibody fragments or derivatives with binding activity for different epitopes of ancrod allows the latter to be neutralized very efficiently.

The novel antibodies, antibody fragments, mixtures or derivatives thereof advantageously have a binding affinity for ancrod in a range from $1\times10^{-7}$ to $1\times10^{-12}$ M, preferably from $1\times10^{-8}$ to $1\times10^{-11}$, particularly preferably from $1\times10^{-9}$ to $5\times10^{-10}$ M.

The novel antidote has an ancrod-neutralizing effect in vivo which is improved, by comparison with goat polyclonal antibodies, by at least 100%, preferably by 250%, particularly preferably by 500%. The monoclonal antibodies also show a distinctly better effect than the polyclonal antibodies in vitro.

Novel monoclonal antibodies or fragments thereof mean in principle all immunoglobulin classes such as IgM, IgG, IgD, IgE, IgA or their subclasses such as the IgG subclasses or mixtures thereof. IgG and its subclasses are preferred, such as $IgG_1$, $IgG_2$, $IgG_{2a}$, $IgG_{2b}$, $IgG_3$ or $IgG_M$. The IgG subtypes $IgG_1/\kappa$ and $IgG_{2b}/\kappa$ are particularly preferred. Fragments which may be mentioned are all truncated or modified antibody fragments with one or two antigen-complementary binding sites which show high binding and neutralizing activity toward ancrod, such as parts of antibodies having a binding site which corresponds to the antibody and is formed by light and heavy chains, such as Fv, Fab or $F(ab')_2$ fragments, or single-stranded fragments. Truncated double-stranded fragments such as Fv, Fab or $F(ab')_2$ are preferred. These fragments can be obtained, for example, by enzymatic means by eliminating the Fc part of the antibody with enzymes such as papain or pepsin, by chemical oxidation or by genetic manipulation of the antibody genes. It is also possible and advantageous to use genetically manipulated, non-truncated fragments.

The antibodies or fragments can be used alone or in mixtures.

The antibody genes for the genetic manipulations can be isolated, for example from hybridoma cells, in a manner known to the skilled worker. For this purpose, antibody-producing cells are cultured and, when the optical density of the cells is sufficient, the mRNA is isolated from the cells in a known manner by lyzing the cells with guanidinium thiocyanate, acidifying with sodium acetate, extracting with phenol, chloroform/isoamyl alcohol, precipitating with isopropanol and washing with ethanol. cDNA is then synthesized from the mRNA using reverse transcriptase. The synthesized cDNA can be inserted, directly or after genetic manipulation, for example by site-directed mutagenesis, introduction of insertions, inversions, deletions or base exchanges, into suitable animal, fungal, bacterial or viral vectors and be expressed in appropriate host organisms. Preference is given to bacterial or yeast vectors such as pBR322, pUC18/19, pACYC184, lambda or yeast mu vectors for the cloning of the genes and expression in bacteria such as E. coli or in yeasts such as Saccharomyces cerevisiae.

The invention furthermore relates to cells which synthesize the novel antibodies. This [sic] may be animal, fungal, bacterial cells or yeast cells after transformation as mentioned above. They are advantagoeusly hybridoma cells or trioma cells, preferably hybridoma cells. These hybridoma cells can be produced, for example, in a known manner from animals immunized with ancrod and isolation of their antibody-producing B cells, selecting these cells for ancrod-binding antibodies and subsequently fusing these cells to, for example, human or animal, for example, mouse mylemoa cells, human lymphoblastoid cells or heterohybridoma cells (Koehler et al., Nature 256, 1975: 496) or by infecting these cells with appropriate viruses to give immortal cells. Hybridoma cell lines produced by fusion are preferred, mouse hybridoma cell lines are particularly preferred, and hybridoma cell lines which secrete the antibodies MAb 1-2, MAb 2-29/3 or MAb 3-27 and which have been deposited at the DSMZ (Deutsche Sammlung für Mikroorganismen und Zellkulturen in Braunschweig) under the numbers DSM ACC2317, DSM ACC2318 and DSM ACC2319 are very particularly preferred.

The abovementioned hybridoma cell lines secrete particularly preferred antibodies of the IgG type. The antibodies MAb 1-2, MAb 2-29/3 and MAb 3-27 which are formed are of the IgG subtypes $IgG_1/\kappa$, $IgG_{2b}/\kappa$ and $IgG_1/\kappa$. These preferred antibodies bind to different epitopes of the ancrod molecule, as has been shown by tests on competitive binding of the antibodies among themselves. The binding of the particularly preferred antibody MAb 1-2 to its epitope results in the most extensive neutralization of the ancrod molecule, and thus the smallest amounts of antibody are required to neutralize the enzymatic effect. The monoclonal antibodies show a distinctly greater neutralizing effect than the antidote which is normally used for treating hemorrhages and is based on polyclonal antibodies which are obtained from goats and are marketed by Knoll AG (Ludwigshafen) as antidote.

Derivatives of the novel monoclonal antibodies which may be mentioned here are peptides, peptidomimetics derived from the antigen-binding regions of the antibodies, and antibodies, fragments or peptides bound to solid or liquid carriers such as polyethylene glycol, glass, synthetic polymers such as polyacrylamide, polystyrene, polypropylene, polyethylene or natural polymers such as cellulose, Sepharose or agarose, or conjugates with enzymes, toxins or radioactive or nonradioactive markers such as 3H, 123I, 125I, 131I, 32P, 35S, 14C, 51Cr, 36Cl, 57Co, 55Fe, 59Fe, 90Y, 99mTc, 75Se, or antibodies, fragments or peptides covalently bonded fluorescent/chemiluminescent labels such as rhodamine, fluorescein, isothiocyanate [sic], phycoerythrin, phycocyanin, fluorescamine, metal chelates, avidin, streptavidin or biotin.

The novel antibodies, antibody fragments, mixtures and derivatives thereof can be used directly, after drying, for example freeze drying, after attachment to the abovementioned carriers or after formulation with other pharmaceutical active and ancillary substances for producing pharmaceutical preparations. Examples of active and ancillary substances which may be mentioned are other antibodies, antimicrobial active substances with a microbiocidal or microbiostatic action such as antibiotics in general or sulfonamides, antitumor agents, water, buffers, salines, alcohols, fats, waxes, inert vehicles or other substances customary for parenteral products, such as amino acids, thickeners or sugars. These pharmaceutical preparations are used to control diseases, preferably to control coagulation disturbances, advantageously disturbances of the peripheral blood system, or for stroke.

The novel antidote can be administered orally or parenterally—subcutaneously, intramuscularly, intravenously or interperitoneally [sic]—and intramuscular or intravenous administration is preferred.

The novel antibodies, antibody fragments, mixtures or derivatives thereof can be used in diagnosis directly or after coupling to solid or liquid carriers, enzymes, toxins, radioactive or nonradioactiven labels or to fluorescent/chemiluminescent labels as described above. In which case [sic] ancrod can be detected in a wide variety of body fluids from a wide variety of organisms such as humans or animals or a wide variety of liquids such as culture media from yeasts, bacteria, fungi or human or animal cell cultures.

EXAMPLES

1. Preparation of the Hybridoma Cell Lines

The immunization, fusion, selection and characterization were carried out by techniques described in the literature (eg. J. H. Peters; Monoklonale Antikörper, Herstellung und Charakterisierung; Springer Verlag; A. M. Campbell; Monoclonal Antibody and Immunosensor Technology; published by Elsevier, chapters 2 to 7 and 8, 1991).

Female Balb/c mice were immunized intraperitoneally with 100 µg of ancrod which had been inactivated in respect of enzymatic activity by crosslinking, in a 2–3 week rhythm in accordance with the following administration scheme:
1. in 100 µl of PBS+100 µl of complete Freund's adjuvant
2. in 100 µl of PBS+100 µl of incomplete Freund's adjuvant
3.–5. in 200 µl of PBS Three days after the last antigen administration, the spleen was removed, the cells were washed and isolated, and the lymphocytes were fused to the myeloma cell line SP2/0-Ag14 (=ATCC CRL 1581). This was done by mixing them in the ratio of 5:1, incubating with 1.5 ml of PEG solution (=polyethylene glycol solution at 37° C. for 1 min and mixing with PBS (=phosphate-buffered saline) (1 ml for 30 sec., 3 ml for 30 sec., 16 ml for 60 sec.). After a washing step, the cells were cultivated in selection medium [DMEM (=Dulbecco's Modified Eagle Medium); 10% FCS (=fetal calf serum); 10% Condimed H1 (Boehringer Mannheim); HAT supplement (=hypoxanthine, aminopterin, thymidine supplement); ITS supplement (=insulin, transferrin, selenite supplement); pyruvat; glutamine; streptomycin/penicillin] at 37° C./7.5% $CO_2$.

Hybridomas specifically secreting anti-ancrod antibodies were identified as follows by means of a specific ELISA in a microtiter plate:

coat microtiter plates with 0.1 ml/well ancrod or reference proteins to determine the specifity (1 µg/ml 0.05 M $NaHCO_3$ pH 9.2) at 4° C. for 16 h saturate with 0.3 ml/well 1% BSA/PBS at 23° C. for 0.5–1 h (h=hour)

wash 3× with PBS/0.05% Tween® 20 incubate with cell culture supernatant (50 µl diluted with 50 µl of PBS/0.1% BSA [=bovine serum albumin)/0.05% Tween® 20) at 23° C. for 2–4 h wash as above incubate with 0.1 ml/well biotinylated anti-mouse IgG antibody in 0.1% BSA/PBS at 23° C. for 2–4 h wash as above incubate with 0.1 ml/well streptavidin-peroxidase complex in 0.1% BSA/PBS at 23° C. for 0.5 h wash as above 0.1 ml/well peroxidase substrate stop the reaction with 0.1 ml/well 2 M $H_2SO_4$ measure the absorption at 450 nm Peroxidase substrate: mix 0.1 ml of TMB solution (42 mM tetramethylbenzidine in DMSO) and 10 ml of substrate buffer (0.1 M Na acetate pH 4.9) then add 14.7 µl of $H_2O_2$.

Hybridomas with a positive antibody reaction were isolated by subcloning and the individual clones were retested. Antibodies with the highest reactivity were employed in the in vitro neutralization assay. It was possible in this way to isolate a large number of positive hybridomas, ie. cells which produce antibodies against ancrod.

2. Production and Characterization of the Monoclonal Antibodies

The monoclonal antibodies were purified from serum-free cell culture supernatants. This was done by transferring the hybridomas stepwise from DMEM/HAT/10% FCS medium via DMEM/HT/10% FCS and DMEM/10% FCS into a serum-free cell culture medium (HT=hypoxanthine, aminopterin) such as SF-3 (Cytogen), PFHM-II (Gibco), HL-1 (Bio Whittaker), Ultra Doma PF (Bio Whittaker) or the like. Protein A-Sepharose and Protein G-Sepharose were used for the subsequent purification by affinity chromatography.

After the cell culture supernatants had been loaded on the chromatography columns, the nonspecifically bound proteins were washed out with 3 M NaCl/1.5 M glycine pH 8.9; the anti-ancrod antibody reactivity was eluted with 500 mM NaCl/0.59% acetic acid.

The antibody subtype was determined in an ELISA similar to that described above but using, in place of the biotinylated anti-mouse IgG antibody, the following biotinylated subtype-specific antibodies: anti-mouse $IgG_1$, anti-mouse IgM, anti-mouse $IgG_{2a}$, anti-mouse κ, anti-mouse $IgG_{2b}$, anti-mouse λ and anti-mouse $IgG_3$.

The antibody types and subtypes of the isolated hybridoma cell lines MAb 1-2, MAb 2-29/3 and MAb 3-27 (see Example 1) were respectively determined as follows $IgG_1/κ$, $IgG_{2b}/κ$ and $IgG_1/κ$.

The affinity constants of the monoclonal antibodies were determined by various techniques disclosed in the literature, such as, for example, eg. [sic] equilibrium dialysis, immunoprecipitation or ELISA (eg. J. H. Peters; Monoklonale Antikörper, Herstellung und Charakterisierung; Springer Verlag; A. M. Campbell; Monoclonal Antibody and Immunosensor Technology; Verlag Elsevier, chapter 11, 1991).

The ELISA method (J. Immunol. Methods 77 (1985) 305–319) revealed the following affinities for natural ancrod (Table I):

TABLE I

Affinities of the monoclonal antibodies for ancrod

| Hybridoma/antibody | $k_D$ |
|---|---|
| MAb 1-2 | $1.7 * 10^{-9}$ |
| MAb 2-29/3 | $3.1 * 10^{-9}$ |
| MAb 3-27 | $4.4 * 10^{-10}$ |

3. "In vitro" Neutralization of Ancrod By Monoclonal Antibodies (=MAbs) Cell Culture Supernatants The neutralizing capacity of the antibodies was quantified by means of the acrod-induced fibrin turbidity. This was done by incubating ancrod and antibodies (cell culture supernatants or purified antibodies) in various ratios of concentrations in BSA-saturated microtiter plates at 37° C. and then adding human fibrinogen (1.5 mg). After incubation at 37° C., the fibrin which was produced was quantified at 340 nm (=optical density=OD).

The ancrod activity could be neutralized as the amount of neutralizing antibodies increased. This was shown by the decreased optical densities (=OD, Table II).

The antibody MAb 1-2 was particularly effective and resulted in complete neutralization even with relatively high ancrod concentrations (Table II, OD corresponds to the blank). The blank in Table II contained all the constituents apart from ancrod. The highest OD values were measured in each case with the various ancrod doses (50, 25 and 12.5 ng/ml ancrod) without addition of the various monoclonal antibodies (Table II).

MAbs 2-29 and 3-27 have affinities for ancrod which are as good as or better than that of MAb 1-2 (Table I), but the antibody-antigen binding resulted in neutralization of the enzymatic activity only with higher antibody doses relative to the amount of ancrod.

TABLE II

Neutralization of ancrod by cell culture supernatants of the MAbs:

| Mixtures | Optical density (= OD) |
|---|---|
| Blank | 0.268 |
| Ancrod 50 ng/ml | 1.45 |
| Ancrod 50 ng/ml + MAb 1-2 | 0.254 |
| Ancrod 50 ng/ml + MAb 2-29 | 1.354 |
| Ancrod 50 ng/ml + MAb 3-27 | 1.133 |
| Ancrod 25 ng/ml | 0.939 |
| Ancrod 25 ng/ml + MAb 1-2 | 0.238 |
| Ancrod 25 ng/ml + MAb 2-29 | 0.333 |
| Ancrod 25 ng/ml + MAb 3-27 | 0.422 |
| Ancrod 12.5 ng/ml | 0.67 |
| Ancrod 12.5 ng/ml + MAb 1-2 | 0.229 |
| Ancrod 12.5 ng/ml + MAb 2-29 | 0.281 |
| Ancrod 12.5 ng/ml + MAb 3-27 | 0.261 |

4. "In vitro" Neutralization of Ancrod By Purified Monoclonal Antibodies

It was possible to evaluate the in vitro neutralizing efficiency of the purified monoclonal antibodies by comparing the 50% neutralization values in the fibrin turbidity assay.

The 50% neutralization value was obtained as follows:

$$\text{OD negative control} + (\text{OD positive control} - \text{OD negative control})/2$$

Negative control: no ancrod added (no fibrin formation)

Positive control: ancrod+fibrinogen (maximum fibrin formation)

Different antibody/ancrod ratios resulted in varying OD values, and the 50% neutralization point was reached with the following antibody concentrations:

|  | MAb 1-2 | Polyclonal antibody | Polyclonal Ab/MAb ratio |
|---|---|---|---|
| Preincubation for 1 hour | | | |
| 1.25 ng of ancrod | 310 ng | 625 ng | 2.0 |
| 2.5 ng of ancrod | 350 ng | 800 ng | 2.3 |
| Preincubation for 2 hours | | | |
| 1.25 ng of ancrod | 80 ng | 310 ng | 3.9 |
| 2.5 ng of ancrod | 150 ng | 650 ng | 4.3 |

It was possible to deduce from the ratios of the amount of antibody required for 50% neutralization that, under the chosen in vitro conditions, the monoclonal antibody MAb 1-2 is better by at least a factor of 2 with preincubation for 1 hour, and by a factor of about 4 with preincubation for 2 hours, than the antidote based on goat polyclonal antibodies.

5. Quantification of Ancrod By Means of a Sandwich ELISA

Ancrod was be [sic] determined in samples for diagnostic purposes, eg. various body fluids, by means of a sandwich ELISA with a combination of two antibodies as shown in the following scheme:

coat the microtiter plates with 5 μg/ml MAb 1-2 or MAb 3-27 in 100 μl/well, diluted in 0.05 M $NaHCO_3$, pH 9.2; 4° C. overnight wash the microtiter plates with PBS/0.05% Tween® 20; 200 μl/well saturate with 300 ml/well 1% BSA/PBS; 23° C. for 0.5 h wash as above 11 standard 2-fold dilutions of ancrod starting with 50 ng/ml in PBS/0.1% BSA/0.05% Tween® 20; 100 µl/well; the samples are employed in parallel in various dilutions; incubate at 23° C. for 2 h wash as above incubate with MAb 2-29; 1 µg/ml diluted in PBS/0.1% BSA/0.05% Tween® 20; 100 µl/well; 23° C. for 2 wash as above incubate with biotinylated anti-mouse $IgG_{2b}$; diluted 1:10000 in PBS/0.1% BSA/0.05% Tween® 20; 100 µl/well; 23° C. for 2 h wash as above incubate with streptavidin-peroxidase complex, diluted 1:10000 in PBS/0.1% BSA/0.05% Tween® 20; 100 µl/well; 23° C. for 0.5 h wash as above add 100 µl/well peroxidase substrate: (mix 10 ml of substrate buffer(0.1 M sodium acetate pH 4.9) with 100 µl of TMB solution (42 mM tetramethylbenzidine in DMSO) and add 14.7 µl of 3% $H_2O_2$)

stop the reaction with 100 µl/well 2 M $H_2SO_4$ measure the absorption at 450 nm It emerged that ancrod is quantifiable and detectable in a concentration range from about 3000 to 100 pg/ml with both the monoclonal antibodies MAb 1-2 and MAb 3-27 and the combinations used. The absolute detection limit is below these quantifiable values (FIG. 1).

6. Competitive ELISA

A competitive ELISA was carried out to characterize the relative position of the MAb binding epitopes on ancrod:

coat microtiter plates with 1 µg/ml ancrod 100 µl/well, diluted in 0.05 M $NaHCO_3$, pH 9.2; 4° C. overnight wash the microtiter plates with PBS/0.05% Tween® 20; 200 µl/well saturate with 300 µl/well 1% BSA/PBS; 23° C. for 0.5 h wash as above 10 ng/ml of each of the biotinylated monoclonal antibodies MAb 1-2-biotin, MAb 2-29/3-biotin and MAb 3-27-biotin were placed in various mixtures in the microtiter plates prepared in this way, and bound to ancrod, and then in each case a different antibody (MAb 1-2, MAb 2-29/3 or MAb 3-27) was added in various concentrations (1 µg/ml–1 ng/ml) depending on the initial antibody to the mixture so that all possible antibody combinations were tested for possible overlaps of their binding sites. The mixtures with the various antibody combinations were incubated in PBS/ 0.1% BSA/0.05% Tween® 20 at 23° C. for two hours and the treated as follows:

wash as above incubate with streptavidin-peroxidase complex, diluted 1:10000 in PBS/0.1% BSA/0.05% Tween® 20; 100 µl/well; 23° C. for 0.5 h wash as above add 100 µl/well peroxidase substrate: (mix 10 ml of substrate buffer(0.1 M sodium acetate pH 4.9) with 100 ml of TMB solution (42 mM tetramethylbenzidine in DMSO) and add 14.7 µl of 3% $H_2O_2$)

stop the reaction with 100 µl/well 2 M $H_2SO_4$ measure the absorption at 450 nm No decrease in the OD was observed in any of the antibody combinations employed, which means that the various monoclonal antibodies did not displace one another on binding to ancrod. They bind to different epitopes on the ancrod molecule. It is therefore possible for more than one of the antibodies to interact with ancrod simultaneously. The various novel monoclonal antibodies can therefore, if necessary and required, be used in combination for rapid and optimal neutralization of the effect of ancrod.

4. In vivo neutralization of ancrod

Ancrod was administered to anesthetized rats by an infusion of 10 IU/kg of body weight into the tail vein for 30 minutes. 10 minutes after starting the ancrod infusion, the various test substances—monoclonal, polyclonal antibodies or placebo—were administered as an intravenous bolus of 1 ml/kg of body weight. Blood samples (8 vol. of blood+2 vol. of 0.11 M citrate anticoagulant) were taken from the carotid artery before and 30 and 60 minutes after starting the ancrod infusion. The plasma was obtained from the citrated blood by centrifugation, and the fibrinogen content was determined by the Clauss coagulation method (calibration plot obtained by adding defined amounts of rat fibrinogen to fibrinogen-free rat plasma).

6 rats were used in each (test substance) group (Table III).

TABLE III

| Test substances and amounts used: | |
|---|---|
| MAb 1-2 | (1.435 mg/kg of body weight) |
| polyclonal Ab | (8.6 mg/kg of body weight; antidote batch A009) |
| polyclonal Ab | (1.5 mg/kg of body weight; antidote batch A009) |

TABLE IV

Measurement of the fibrinogen concentration with the various antibodies

| | Fibrinogen conc. [mg/dl] | | | |
|---|---|---|---|---|
| Time [min] | Ancrod + control | Ancrod + MAb 1-2 | Ancrod + polycl. Ab 8.6 mg/kg | Ancrod + polycl. AK 1.5 mg/kg |
| 0 | 289.7 | 263.4 | 292.4 | 281.8 |
| 30 | 63.8 | 155.9 | 129.0 | 91.5 |
| 60 | 32.1 | 152.7 | 164.0 | 55.8 |

It emerged that MAb 1-2 was able, in the concentration of 1.435 mg/kg of body weight used, to stop a further decline in the fibrinogen level 30 minutes after starting the ancrod infusion. 8.6 mg/kg of body weight are required for the same effect with goat polyclonal antibodies. In a concentration of 1.5 mg/kg of body weight, ie. comparable to the concentration of MAb 1-2, the antidote based on polyclonal antibodies showed no effect (see control in Table IV).

It was possible to deduce on the basis of the fibrinogen concentrations resulting after 60 minutes that the in vivo neutralization under the test conditions by MAb 1-2 was a factor of about 6 better than that by the polyclonal antidote. The neutralizing effect of MAb 1-2 is presumed to be even greater.

We claim:

1. A monoclonal antibody, antibody fragment, mixture or derivative thereof, which binds to ancrod and inhibits its activity, said monoclonal antibody having a binding affinity of at least $1.7 \times 10^{-9}$ M and a 50% neutralization value of about 310 ng as determined in a fibrin turbidity assay with a pre-incubation of 1.25 ng ancrod for 1 hour.

2. A monoclonal antibody, antibody fragment, mixture or derivative thereof as claimed in claim 1, wherein the antibody is of the IgG class.

3. A monoclonal antibody, antibody fragment, mixture or derivative thereof as claimed in claim 1, which is the antibody MAb 1-2, MAb 2-29/3 or MAb 3-27 or mixture thereof.

4. A cell which expresses a monoclonal antibody, antibody fragment, mixture or derivative thereof as claimed in claim 1.

5. A cell as claimed in claim 4, which is from a hybridoma cell line.

6. A cell as claimed in claim 4, wherein a hybridoma cell line is DSM ACC2317, DSM ACC2318, or DSM ACC2319.

7. A pharmaceutical preparation comprising a monoclonal antibody, antibody fragment, mixture or derivative thereof as claimed in claim 1.

8. Compositions for treating coagulation disturbance in a patient undergoing Ancrod therapy comprising a monoclonal antibody, antibody fragment, mixture or derivative thereof as claimed in claim 1.

9. A process for diagnosing a disease caused by inappropriate ancrod concentration in body fluids, said process comprising the step of detecting ancrod levels in body fluids directly or after coupling to solid or liquid carriers, enzymes, toxins, radioactive or nonradioactive labels or to fluorescent or chemiluminescent labels a monoclonal antibody, antibody fragment, mixture or derivative thereof as claimed in claim 1.

10. A process as claimed in claim 9 wherein said step of detecting the ancrod is made in culture media.

* * * * *